United States Patent
Harry et al.

(10) Patent No.: US 7,349,739 B2
(45) Date of Patent: Mar. 25, 2008

(54) METHOD AND APPARATUS FOR NEUROPHYSIOLOGIC PERFORMANCE

(75) Inventors: Jason D Harry, Rumford, RI (US); Stephen J Kleshinski, Scituate, MA (US); James B Niemi, West Kingstown, RI (US); Gregg R Draudt, Stowe, MA (US); Dirk Ahlgrim, Boston, MA (US); James J. Collins, Newton, MA (US)

(73) Assignee: Afferent Corporation, Providence, RI (US)

( * ) Notice: Subject to any disclaimer, the term of this patent is extended or adjusted under 35 U.S.C. 154(b) by 252 days.

(21) Appl. No.: 10/429,252

(22) Filed: May 5, 2003

(65) Prior Publication Data
US 2004/0073271 A1   Apr. 15, 2004

Related U.S. Application Data

(60) Provisional application No. 60/377,202, filed on May 3, 2002.

(51) Int. Cl.
*A61N 1/18* (2006.01)
(52) U.S. Cl. .......................................... 607/49; 607/48
(58) Field of Classification Search .................... 607/2, 607/48, 49, 50, 46
See application file for complete search history.

(56) References Cited

U.S. PATENT DOCUMENTS

| 792,162 A | 6/1905 | Potter |
| 3,881,495 A | 5/1975 | Pannozzo et al. |
| 4,105,017 A | 8/1978 | Ryaby et al. |
| 4,308,868 A | 1/1982 | Jhabvala |
| 4,664,118 A * | 5/1987 | Batters ........................ 607/46 |
| 4,774,967 A | 10/1988 | Zanakis et al. |
| 4,811,742 A * | 3/1989 | Hassel et al. ............... 600/546 |
| 4,919,140 A | 4/1990 | Borgens et al. |
| 5,487,759 A | 1/1996 | Bastyr et al. |
| 5,782,873 A * | 7/1998 | Collins .......................... 607/2 |
| 6,032,074 A * | 2/2000 | Collins .......................... 607/2 |
| 6,065,154 A | 5/2000 | Hulings et al. |
| 6,095,148 A | 8/2000 | Shastri et al. |
| 6,104,956 A | 8/2000 | Naritoku et al. |
| 2002/0087201 A1* | 7/2002 | Firlik et al. ................... 607/45 |
| 2004/0147975 A1* | 7/2004 | Popovic et al. ............... 607/48 |

OTHER PUBLICATIONS

Shier, D., Butler, J. and Lewis, R., Hole's Human Anatomy and Physiology (Ninth Edition), McGraw-Hill 2002, pp. 456-457.*

(Continued)

*Primary Examiner*—Angela D Sykes
*Assistant Examiner*—Alyssa M. Alter
(74) *Attorney, Agent, or Firm*—Nixon Peabody LLP; Donald R. Studebaker

(57) ABSTRACT

The invention features methods and apparatus for enhancing neurophysiologic performance, such as sensorimotor control and neuroplasticity. A preferred method involves inputting bias signals to sensory cells of a subject, thereby improving sensory cell function, while the subject is performing a predefined physical activity. A system used to practice the method of the invention includes a wearable device to which is secured at least one repositionable signal input device and a signal generator that is communicatively coupled to the signal input devices.

101 Claims, 6 Drawing Sheets

OTHER PUBLICATIONS

Prizm Medical Inc., http://www.prizm-medical.com, prizm product: Electro TM garment.*

Merriam-Webster Online Dictionary, htp://webster.com, defined: sensorimotor.*

Dimitijević M.M. Mesh-glove. 1. A method for whole-hand electrical stimulation in upper motor neuron dysfunction, Scand J Rehabil Med, Dec. 1994; 26 (4):183-186.*

Popovic et al. Neurorehailitiaon of Upper Extremities in Humans with Sensory-Motor Impairments, Neuromodulation, 2002; 5 (1) 54-67.*

Kraft et al., Techniques toImproves Function of the Arm and Hand in Chronic Hemiplegia, Arch Phys Med Rehabil, 1992; vol. 73; 220-258.*

Benzi et al., "Noise in Human Muscle Spindles", Nature, vol. 383, pp. 769-770, Oct. 31, 1996.

Glanz, "Sharpening the Senses With Neural 'Noise'" Science Magazine, vol. 277, No. 5333, Issue of Sep. 1997, p. 1759.

Laskowski et al., "Refining Rehabilitation With Proprioception Training: Expediting Return to Play", The Physician and Sportsmedicine, vol. 25, No. 10, Oct. 1997.

McCall et al., "Muscle Afferent-Pituitary Axis: A Novel Pathway for Modulating the Secretion of a Pituitary Growth Factor", Exercise and Sport Sciences Review, vol. 29, No. 4, pp. 164-169, 2001.

Wesenfeld et al., "Noise-Enhanced Tactile Sensation", Scientific Correspondence, Nature, vol. 383, p. 770, Oct. 31, 1996.

Wong et al., "Rapid Dendritic Movements During Synapse Formation and Rearrangement", Current Opinion in Neurobiology 2000, vol. 10, pp. 118-124.

* cited by examiner

METHOD AND APPARATUS FOR NEUROPHYSIOLOGIC PERFORMANCE

RELATED U.S. APPLICATION DATA

This application is a non-provisional application of U.S. provisional patent application No. 60/377,202.

BACKGROUND OF THE INVENTION

1. Field of the Invention

This invention relates to methods and apparatus for enhancing neurophysiologic performance, such as sensorimotor control and neuroplasticity, by combining improved function of sensory cells with pre-defined physical activity and use of certain devices.

2. Description of Related Art

The nervous system of mammals is a complex set of interrelated and interacting sub-systems. The sub-systems are categorized and named both by their anatomic positions and by their function. At the highest level, the nervous system is divided into central and peripheral nervous systems. The central nervous system (CNS) is comprised of the brain and spinal cord; the peripheral nervous system (PNS) subsumes all the remaining neural structures found outside the CNS. The PNS is further divided functionally into the somatic (voluntary) and autonomic (involuntary) nervous systems. The PNS can also be described structurally as being comprised of afferent (sensory) nerves, which carry information toward the CNS, and efferent (motor) nerves, which carry commands away from the CNS.

Interconnections between afferent and efferent nerves are found in the spinal cord and brain. Taken together, certain groupings of afferent and efferent nerves constitute sensorimotor "loops" that are required to achieve coordinated movements in the face of perturbations from the environment and changes in volitional intent. In the periphery (trunk, upper extremities, and lower extremities), afferent nerves carry sensory information arising from special neurons that are sensitive to pain, temperature, and mechanical stimuli such as touch and vibration at the skin surface, and position, force, and stretch of deeper structures such as muscles, tendons, ligaments, and joint capsule. The term "proprioception" generally applies to sensory information directly relevant to limb position sense and muscle contraction. Combined with tactile (touch) sensation, mechanical sensory information is collectively known as "somatosensation."

Specialized "mechanoreceptor" neurons transduce mechanical stimuli from the body's interaction with the environment into electrical signals that can be transmitted and interpreted by the nervous system. Pacinian corpuscles in the skin fire in response to touch pressure. Muscle spindles, found interspersed in skeletal muscle tissue, report on the state of stretch of the surrounding muscle. Golgi tendon organs sense the level of force in the tendon. Free nerve endings in structures surrounding joints (ligaments, meniscus, etc.) provide additional information about joint position. Some of these mechanoreceptor systems are thought to interact directly via excitatory and inhibitory synapses and descending pathways to modulate the performance or interpretation of signals from other mechanoreceptor systems.

Sensory cells of all types are typically threshold-based units. That is, if the stimulus to a sensory cell is of insufficient magnitude, the cell will not activate and begin signaling. Such a stimulus is called "subthreshold." A stimulus that is above the threshold is called "suprathreshold."

Connections within the nervous system—brain, spinal cord, and peripheral nerves—are highly changeable in the face of demands placed on the body: new forms of activity, pathologies, and injuries. In healthy individuals, these neurological changes allow for the acquisition of new physical skills, a process termed "motor learning." Following certain types of soft tissue injury (e.g. rupture of the anterior cruciate ligament of the knee, a structure known to be rich in mechanoreceptors), and subsequent medical efforts such as surgery used to repair the damage, the nervous system can undergo compensatory changes to accommodate for loss of the natural sensory neurons. Similar PNS and CNS nervous system changes account for some individual's ability to regain lost motor function following spinal or brain injuries. Taken together, these structural changes in the nervous systems are termed "neuroplasticity" or "neuroplastic changes."

Recent research has established that afferent (sensory) activity from the periphery is one of the key drivers of neuroplastic changes in the nervous system, both in the PNS and CNS.

The present invention focuses on mechanical sensory neurons in the periphery and the role they play, specifically, in sensorimotor control and in inducing neuroplastic changes in the nervous system. In this invention, we combine prior art methods of improving the performance of individual sensory cells with novel methods and apparatus to achieve improvements in sensorimotor control and neuroplasticity. Importantly, the nature of the improved sensory cell performance is that the natural firing rate in response to environmental stimuli is increased in an information-rich fashion. That is, the increased sensory cell firing is concordant with limb function and hence is not gratuitous or uncoordinated in nature.

Electrical stimulation of tissue has been used for various therapeutic purposes including stimulating muscle activity, relieving pain, and producing sensation. The sequence of effects produced by electrical stimulation, as its intensity is increased, generally follows a pattern of a perception of an electrical sensation (such as tingling), an increase in sensation, fasciculation muscle contraction, pain, and then injury in the form of electrical burns or cardiac arrhythmias.

In the past, pulsed electrical waveforms having an adjustable pulse duration, intensity and pulse width have been applied to a particular area of the human body for therapeutic purposes to suppress pain. Electrical waveform therapy, such as that disclosed in U.S. Pat. No. 5,487,759 to Bastyr, et al. has been used for symptomatic relief and management of chronic, post surgical and posttraumatic acute pain and for inducing muscle contraction for the retardation of atrophy.

Stimulation below perception levels (i.e. subthreshold stimulation) used to enhance the function of sensory cells is described in U.S. Pat. Nos. 5,782,873 and 6,032,074 to Collins, the entire contents of which are incorporated by reference. Collins discloses a method and apparatus for improving the function of sensory cells by effectively lowering their threshold of firing. Briefly, a subthreshold stimulation, or "bias signal," is input to the sensory neuron that predisposes the neuron to firing, without actually causing it to fire. In one preferred embodiment, the bias signal is a broadband signal containing many frequencies, often termed "noise." Since sensory cells are typically threshold-based units, lowering the sensory cell threshold decreases the level of outside stimulus needed to cause the sensory cell to respond (i.e. fire). Thus, the sensory cell, in the presence of the bias signal, is expected to respond to stimulus intensities that would normally be considered subthreshold to the neuron in the absence of noise. Both electrical and mechanical modalities of bias signal, used individually or in combination, may be used to effect the lowering of sensory neuron detection threshold.

SUMMARY OF THE INVENTION

In a preferred embodiment, provided is a method of enhancing sensorimotor performance in a subject comprising inputting at least one bias signal to at least one sensory cell area of a subject while the subject is performing a pre-defined physical activity which utilizes sensory cells within the sensory cell area and which are involved in the sensorimotor performance to be enhanced. By inputting the bias signal in accordance with this method the function of the sensory cells is improved. In combination with physical activity, enhancements to sensorimotor performance result. Enhancements effectuated using the method of the present invention include, for example: improved joint stability, improved gait, improved balance, improved motor learning, and improved motor skill.

The bias signal applied to the subject may modulated in response to a measured physical variable measured from at least one body segment of the subject during the pre-defined physical activity. The physical variable is selected from force, pressure, position, angle, velocity, and acceleration. The bias signal may also be modulated in synchrony with the pre-defined activity. In a preferred embodiment, the bias signal is a mechanical or an electrical signal. The preferred displacement of mechanical signals is about 1 μm to about 10 mm. The frequency of the mechanical signals is preferably within the range of about 0 Hz to about 1000 Hz. The current density of electrical signals is preferably in the range of about 1 $\mu A/in^2$ to about 1000 $\mu A/in^2$. The frequency of the electrical signal is preferably within the range of about 0 Hz to about 10,000 Hz.

In yet another embodiment, provided is a system for enhancing sensorimotor performance in a subject. The system is preferably comprised of a wearable device and a signal generator. At least one repositionable input signal device is secured to the wearable device. The signal generator is communicatively coupled to the signal input device and includes a power source, a signal processor, and a controller. The signal generator may be repositionable and removably attached to the wearable device. The signal processor may include a calibration module for adjusting the bias signal produced by the signal processor. The wearable device preferably forcibly presses the signal input device to the subject's skin surface. To this end, the wearable device is preferably constructed from stretchable fabrics or materials. Furthermore, the signal input device is electrically connected to the signal generator. The means by which the signal input device is electrically connected is preferably housed within, and thereby protected by, the structure of the wearable device.

In addition to improved sensorimotor performance, improvements in neuroplasticity and an increase in growth hormone production can be achieved using the method and apparatus of the present invention.

DETAILED DESCRIPTION OF THE PREFERRED EMBODIMENTS

The preferred embodiments of the present invention provide a method and system for improving sensorimotor performance of humans, non-human mammals, and non-mammalian animals, hereinafter termed "subjects." Improvements in sensorimotor performance are meant to include immediate or acute effects, such as improved dynamic joint stability, and more durable effects as would result from neuroplastic changes in the PNS or CNS. The method comprises inputting a bias signal to sensory cells of the subject, so as to improve the function of those sensory cells by effectively lowering their threshold of firing, while the subject engages in pre-defined physical activity. Acting in conjunction with this preferred method is a preferred apparatus that comprises a wearable device and other electromechanical components that provide a convenient and secure means of delivering the bias signal to the subject. As used herein, the term "bias signal" will be taken to mean a subthreshold form of stimulation to a sensory neuron, whether electrical or mechanical in nature, whose waveform may be periodic, aperiodic, deterministic, or non-deterministic and may contain one or many frequencies.

The method and system according to the preferred embodiments of the present invention are useful, for example, to enhance sensorimotor function in healthy individuals as well as in individuals with disorders, diseases and/or injuries. For example, the method and system could be used by healthy individuals striving to learn a new motor skill, such as might be required for athletic activity. In another example, the method and system could be applied to individuals with elevated sensory thresholds or other neurological dysfunction, such as might arise from aging, peripheral neuropathies, or strokes.

Figure 1:
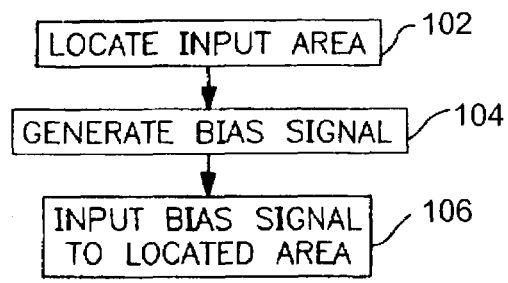
FIG. 1 is a flow chart of a method for enhancing the function of a sensory cell.

FIG. 1 is a flow chart of a method for enhancing the function of a sensory neuron according to one embodiment of the present invention. In step 102, an area associated with the sensory cell whose function is to be enhanced and to which a bias signal is to be input is located. The located area is hereinafter referred to as the input area. Once the input area has been located, the bias signal is generated in step 104. Then in step 106, the bias signal is input to the input area so as to effectively lower the threshold of sensory cells with which the input area is associated.

Figure 2:
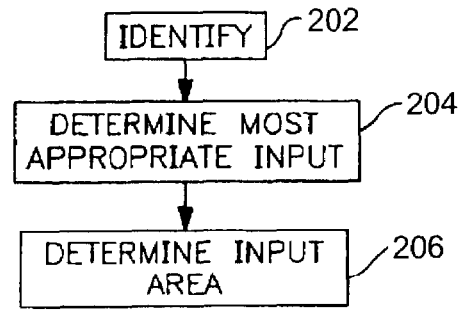
FIG. 2 is a flow chart of a method of locating an input area.

FIG. 2 is a flow chart showing one embodiment of locating an input area according to step 102. Locating the input area depends, inter alia, on the sensory system whose function is to be improved and the method by which a bias signal may be input to sensory cells associated with the sensory system. Step 202 is a preliminary step in which an identification scheme is undertaken to identify a particular sensory system whose function is to be enhanced. The identification scheme, to some extent, depends on the cooperation of the individual. That is, this step is similar to a diagnosis, however, the individual need not be suffering from any disease or disorder to be subject to the enhancement process contemplated herein. In one embodiment, the sensory system whose function is to be enhanced is one whose function has been degraded by disease.

In an alternative embodiment, the sensory system to be enhanced is one that functions normally. In step 204, the most appropriate way of inputting a bias signal to the target sensory system is determined. The most appropriate input means depends on a number of factors including, the target sensory system, the nature of the transduction system for the target sensory system, the present state of the target sensory system (i.e., whether it is impaired or in any way dysfunctional), and the nature of the signal which is to be determined (e.g., the amplitude and frequency content of the signal). Input means that are appropriate in certain circumstances include, but are by no means limited to, nerve cuffs, implanted electrodes, surface electrodes, muscle stimulators, tendon stimulators and magnetic field stimulators.

Once the most appropriate input means is determined in step 204, the input area is determined in step 206. The location of an input area depends on the same factors as the determination of the most appropriate input means. The location of the input area, however, varies for a particular input means depending on, among other factors, whether the target sensory system is in any way dysfunctional, the cause and location of any such dysfunctionality, and the nature of the stimulator to be used. More specifically, if a dysfunctionality caused by some physical damage to sensory cells is present in the sensory system, it may be necessary to locate the input area such that the bias signal will bypass the physical damage causing the dysfunctionality. Further, the fact that some stimulators, e.g. implanted electrodes, may require invasive procedures while others, e.g., surface electrodes, require only non-invasive procedures is also a factor to consider.

Figure 3:
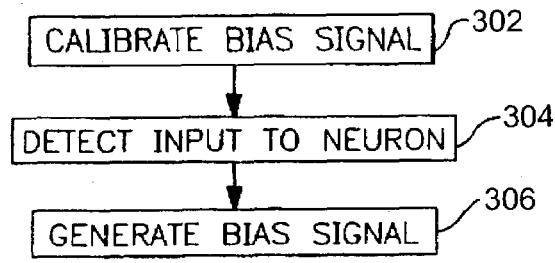
FIG. 3 is a flow chart of a method of generating a bias signal.

Once the input area is determined and the input means installed, the bias signal to be input is generated. FIG. 3 shows one embodiment of a method of generating a bias signal. In an initial step 302, the bias signal is calibrated. That is, an optimal level for the bias signal is determined. Depending on the determinations of steps 204 and 206, there exists a particular form of bias signal for which the signal detection ability of a given neuron in the target sensory system is optimally enhanced. For example, a bias signal having parameters with certain predetermined values will give rise to optimal enhancement. Calibration helps to ensure that certain parameters of the bias signals generated will be adjusted to achieve optimal enhancement. Examples of signal parameters of the bias signal that may be calibrated are amplitude, frequency, offset (D.C. bias), intensity, variance, frequency bandwidth and spectral characteristics in general. Calibration is typically accomplished prior to installation of the enhancement system and may be accomplished intermittently while the enhancement system is installed. If calibration is to take place while the enhancement system is installed, then it is desirable to install the enhancement system so it is accessible from the outside of the body so that calibration may be accomplished non-invasively.

In one embodiment, the calibration is accomplished by inputting an input signal of interest to a sensory cell coupled with a bias signal produced by the enhancement system. The response of the sensory cell to the combined input is recorded as a function of a parameter of interest in the bias signal. That is, the response of the sensory cell is recorded as a parameter of interest in the bias signal is modulated. Using the recorded results, the coherence between the combined input and the response of the sensory cell is then characterized by computing some measure such as the cross-correlation coefficient described below. The response of the sensory cell is maximally enhanced when the coherence measure is maximized. This maximally enhanced response corresponds to some value or range of values of the bias signal parameter of interest that can be determined by, for example, examining a record of the bias signal. Thus, an optimal value or range of values for the parameter of interest of the bias signal is determined. The process can be repeated using other input signals and parameters of interest thereby determining a bias signal with optimal parameters for input signals with varying parameters.

According to one embodiment of the present invention, the bias signal is optimized by examining the cross-correlation coefficient, $C_1$:

$$C_1 = \frac{C_0}{\sqrt{\overline{S^2(t)}} \sqrt{\overline{(R(t) - \overline{R(t)})^2}}}$$

where $$C_0 = \overline{S(t)R(t)}$$

where $S(t)$ is the input signal, $R(t)$ is the output of the sensory neuron or sensory system (e.g., the neural mean firing rate signal or the neural spike train), and the overbar denotes an average over time. $S(t)$ and $R(t)$ can be measured with any appropriate transducers, for example, a needle electrode may be used to measure the output of a neuron. Maximizing $C_1$ corresponds to maximizing the coherence between the input signal $S(t)$ and the neuron's output $R(t)$. The value of $C_1$ for a given input signal will depend upon the parameter of interest of the bias signal. Thus, a bias signal having parameters which will produce the desired output $R(t)$ may be determined.

The results of the calibration process may be utilized, for example, by modulating the bias signal in response to an input signal or by determining a set of parameter values which, on average, will achieve optimal enhancement for any input signal. In the first instance, parameter values for the bias signal are, for example, tabulated against parameters of the input signal. Upon occurrence of an input signal, certain parameters of the input signal are measured, and a bias signal having corresponding parameter values is generated by, for example, referencing the tabulated results. In this way, the bias signal is modulated or optimized for each particular input signal. In the second instance, a single set of parameter values which will achieve optimal enhancement for most signals is calculated and used to generate a bias signal which is for use in response to every input.

After the input device has been calibrated and installed, in one embodiment, an input signal to the neuron is detected. As will be explained in conjunction with FIG. 4, one embodiment of a system for enhancing the function of a sensory neuron includes signal detection capabilities, for example, a transducer and signal processor. Thus, in step 304, input signals to the neuron are detected using the signal detection capabilities.

Once an input signal is detected in step 304, a bias signal is generated in step 306. As explained above with respect to the calibration process, the bias signal has either parameters which are modulated depending on certain parameters of each input signal or a constant, non-modulated, set of parameters which are designed to optimally enhance the function of a sensory cell in response to most input signals. If a bias signal having a non-modulated set of parameters is used, then a somewhat simpler input system is used. In general, the nature of the bias signal to be used, that is, modulated or non-modulated, depends on the nature of the sensory system to be enhanced. Once the bias signal is generated, it is input to the neuron in step 106.

In the embodiments described above, a bias signal is produced only in response to the detection of an input signal to the neuron. In an alternative embodiment, after the input device has been calibrated and installed, a bias signal is continuously generated and input to the neuron. That is, an input signal does not need to be detected. In a method according to this embodiment, the bias signal is either modulated or non-modulated. If the bias signal is modulated, then the continuously generated bias signal is modulated as described above, when an input signal is detected. If a non-modulated bias signal is used in this embodiment, then a simplified input system may be used. As discussed above, whether a modulated or non-modulated bias signal is used depends upon, inter alia, the nature of the system to be enhanced.

In another embodiment, a distributed enhancement process is used. In this embodiment, the enhancement process described above is modified such that a bias signal is generated and input to neurons at a plurality of locations to stimulate an array of sensory cells and thereby provide a distributed enhancement effect. In this distributed enhancement system, as above, either a continuous or non-continuous, and modulated or non-modulated bias signals may be used. As one example, if the sensory function of the urinary tract is to be enhanced, a bias signal may be input to a number of distributed points around the bladder so that improved fullness sensation is obtained.

Figure 4:
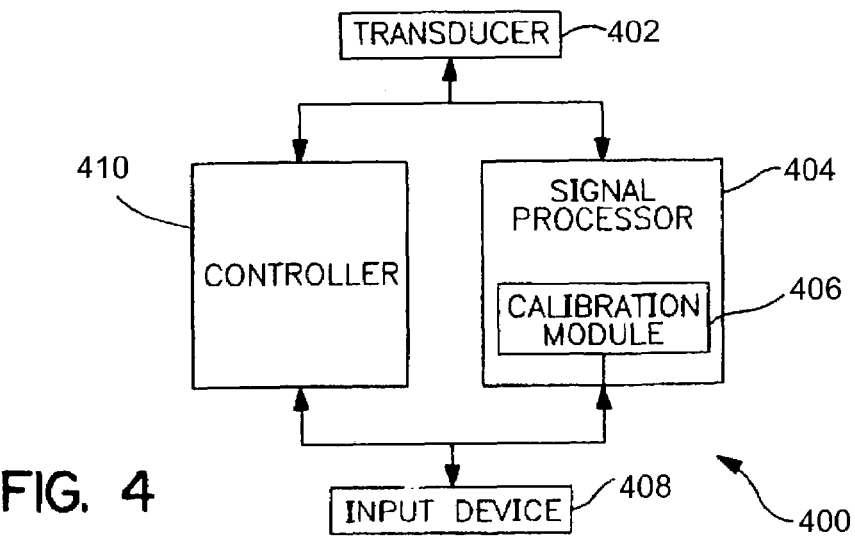
FIG. 4 is a schematic depiction of a system for enhancing the function of a sensory cell.

One embodiment of an enhancement system 400 for implementing the method for enhancing the function of a sensory neuron is shown in FIG. 4. Enhancement system 400 comprises a transducer 402, a signal processor 404, an input device 408 and a controller 410. Enhancement system 400 operates on electrical signals. An input signal to a sensory cell is typically initiated by contact with the outside world which contact is generally not in the form of an electrical signal. An input signal might be initiated by, for example, a touch, a movement of a body segment, a sound wave or light. One function of transducer 402 is to detect input signal initiating contacts and convey the contact to enhancement system 400 generally and signal processor 404 specifically. Another function of transducer 402 is to convert an input signal initiating contact into a signal in a form that is usable by enhancement system 400. The mechanism used for transducer 402 depends on the sensory system targeted. As an example, if the auditory system is being targeted for enhancement, transducer 402 may take the form of a stimulating electrode or an array of stimulating electrodes arranged in the vicinity of the ear. As another example, if the proprioceptive system is being targeted for enhancement, transducer 402 is a tendon stimulator, implemented by way of a piezoelectric transducer, installed or attached via elastic straps to a tendon or parent muscle associated with the sensory cells whose function is to be enhanced. As still another example, if the vibration or touch-pressure sensation system is being targeted for enhancement, transducer 402 is a surface electrode installed or applied over the skin of the area of the body containing the cells to be stimulated. Such an electrode is attached using flexible electrode/skin interfaces.

Signal processor 404 produces a bias signal to be input to the sensory system targeted for enhancement through input device 408. Signal processor 404 is electrically connected to transducer 402, input device 408 and controller 410. As discussed above, a bias signal may be either continuous or non-continuous and modulated or non-modulated. The form of signal processor 404 depends upon the desired form of the bias signal to be produced. In one embodiment, where a non-continuous, modulated bias signal is desired, signal processor 404 preferably includes both signal detection capabilities and look-up table capabilities to store parameter values for the bias signal. In another embodiment, where a constant, non-modulated bias signal is desired, signal processor 404 does not necessarily require signal detection capabilities and look-up table capabilities. In one embodiment, signal processor 404 is either a special function IC or a general micro-processor and is preferably small, lightweight and portable. Further, signal processor 404 preferably includes signal conditioning and data acquisition abilities. In one embodiment, a PCMCIA chip or card is used as signal processor 404.

Signal processor 404 also includes calibration module 406. Calibration module 406 enables adjustment of the bias signal produced by signal processor 404. For example, for optimal enhancement, signal processor 404 produces a bias signal having predetermined parameters (for example, a predetermined amplitude and frequency) in response to a particular signal received from transducer 402. If these predetermined parameters of bias signal are not properly adjusted, the bias signal will not optimally enhance the function of the targeted sensory system. Calibration module 406 enables these predetermined parameters to be adjusted so that an optimal bias signal is produced. Calibration is typically accomplished prior to installation of enhancement system 400 and may be accomplished intermittently while enhancement system 400 is installed. If calibration is to take place while enhancement system 400 is installed, then it is desirable to install signal processor 404 so it is accessible from the outside of the body so that calibration may be accomplished non-invasively. In an alternative embodiment, signal processor 404 is provided with remote access capability enabling calibration to take place non-invasively whether or not signal processor is accessible from outside of the body.

Input device 408 conveys the bias signal produced by signal processor 404 to the targeted sensory system. Depending on what the targeted sensory system is, input device 408 might take a number of different forms as discussed above. Input devices that are appropriate in certain circumstances include, nerve cuffs, implanted electrodes, surface electrodes, muscle stimulators, tendon stimulators, and magnetic field stimulators. The manner in which input device 408 conveys the bias signal to the targeted sensory system depends on the form of input device 408 and the targeted sensory system. For example, a nerve cuff or implanted electrode is suitable for use when the urinary tract is the targeted sensory system and is typically implanted surgically and conveys the bias signal to the sensory components of the system. A muscle or tendon stimulator, on the other hand, is more suited to mechanically stimulate the proprioceptive system. Such a stimulator mechanically stimulates the proprioceptive system by vibrating a muscle or tendon associated with that system, for example a muscle in the vicinity of a joint. Muscle or tendon stimulators can be applied non-invasively using, for example, an elastic band. In one embodiment, where the targeted sensory system is the vibration or touch-pressure sensation system, a surface electrode-based system is used as input device 408. Specifically, the glove electrode, the sock electrode, and the sleeve electrode, sold under the name ELECTRO-MESH [™] may be used as input device 408. The surface electrode system is placed over the body part of interest, e.g., the hand or foot. Still further, input device 408 may be a magnetic field stimulator used either non-invasively or invasively. For example, a magnetic field stimulator may be used to stimulate cutaneous sensory neurons by positioning the stimulator on the exterior of the body in the vicinity of the sensory cells to be stimulated using elastic bands. A magnetic field stimulator may be used invasively, for example, by surgically implanting the stimulator to stimulate sensory neurons in the area of the bladder.

Controller 410 controls interaction between transducer 402, signal processor 404 and input device 408. The implementation for controller 410 depends upon, among other things, the form of bias signal desired. That is, where a non-continuous, modulated bias signal is desired, controller 410 may be implemented using a microprocessor. In a simpler embodiment, where a continuous, non-modulated bias signal is desired, controller 410 may be implemented using a switch that simply activates the enhancement signal. Alternatively, signal processor 404 may be adequate, so that controller 410 is unnecessary for such an embodiment. By way of example only, controller 410 comprises a microprocessor with suitable programming, or any digital controller. In one embodiment, controller 410 is implemented with the aforementioned PCMCIA chip or card.

The nature and amplitude of the bias signal is controlled in accordance with the type of sensory cell to which the bias signals are applied. Repetitive waveform, pulse or DC signals of the type typically used for other types of injury treatment (e.g. pain suppression, bone healing) are often be avoided in the practice of the present invention, as sensory cells can adapt to simple deterministic signals thereby reducing or eliminating over time the effect of such signals on the sensory cells. Instead, in accordance with the invention, non-deterministic noise signals, such as random, aperiodic noise signals, or recorded repetitions of noise signals are preferably used, so that the sensory cells do not adapt to the noise signals over the extended period of noise signal application that occurs during a physical training regimen. These signals can be continuously generated signals such as those created by known instruments, including a computer random number generator, a noise diode, or thermal noise from a resistor or other electrical component. Sampled signals, such as signals stored in a storage device (RAM, ROM, etc.), or periodically recorded noisy signals, may also be employed.

The sensory cell areas containing neurons to be affected by bias signals may be found at different depths in the human body, causing different signal transmission filtering characteristics to exist between certain of the sensory cells and the signal input device. In a preferred embodiment, the bias signal can be combined with other signal types to overcome this problem. For example, a chirped signal can be formed by overlaying a noise signal with a swept frequency signal that regularly sweeps through a signal frequency range. This combined signal may be tailored to permit the amplification of frequency ranges that are normally attenuated by transmission in the body. Thus, the signal is compensated at the skin-surface level for expected attenuations that would occur prior to it reaching the target sensory cell. This technique might also be used to reduce the effort required to determine an efficacious signal since it might contain all desired frequency ranges.

Another method of the present invention involves enhancing various neurophysiologic functions by applying an externally produced bias signal to a sensory cell area, as described above, while the subject is performing a predefined physical activity. Neurophysiologic functions enhanced by this method of the present invention include, for example, limb position sense enhancement, increase release of growth hormones, enhanced peripheral neuroplastic changes, and enhanced central, including cortical, neuroplastic changes.

Most physical training regimens are undertaken to induce, among other things, motor learning, i.e. the acquisition of new motor skills or the regaining of motor skills that have been lost due to injury or disease. To achieve the aforementioned sensorimotor performance enhancements, while a subject performs a specified physical activity bias signals are applied to sensory cells involved in the specific physical activity to lower the threshold at which such cells are triggered by the external stimuli resulting from the activity. By making the sensory cells more responsive, the number of action potentials produced for any given amount of external stimuli is increased, thereby improving the rate and/or quality of motor learning resulting from the activity.

Coordinated motion of the extremities, for example, requires precise interplay between descending volitional signals from the brain, muscle contraction, limb movement, and interaction with the environment. This tight control is reliant, in part, on sensory feedback of a mechanical nature from the extremities involved in the motion. Somatosensory information, e.g. tactile information from foot sole and proprioceptive information from knee joint, is clearly important both to normal gait and to more vigorous activities such as jumping and landing. The method of the present invention is effective to boost coordinated sensory information from the mechanoreceptors involved in limb position sense during movement of the extremities. This added information content during movement provides a means for improved sensorimotor control. Such improvements result in enhanced balance, corrected gait patterns, and prevention of injuries by avoiding, for example, hyperextension of joints.

In one embodiment of the invention, a bias signal is provided during a training regimen to a plurality of structures that participate in stability of a joint in a subject, to thereby promote joint sensation and feedback to enhance stability in the subject. For example, at least one input device, e.g. an electrode, can be placed at or near the articular space such that sensory cells in or adjacent to the ligaments, the joint capsule and meniscus, are stimulated. The bias signal is provided at a level below the perception threshold of the sensory cells associated with the structures as well as below the cutaneous pain threshold.

In another preferred embodiment, the bias signal can be provided to at least two structures that maintain joint stability and are on opposite sides of the joint such that the performance of the sensory cells contained in these structures are enhanced. Preferably, a bias signal is provided at or adjacent to the joint and at least two different antagonist muscles on opposite sides of a joint where the action of these muscles determines the relative flexion and extension of the joint.

The bias signal can be provided simultaneously to each of the structures or it can occur sporadically at each of the structures. Preferably, the bias signal is repeatedly provided to each of the structures, e.g., the bias signal is repeated such that the bias signal is simultaneously provided to each of the structures or the bias signal is repeated such that the bias signal is sporadically provided to each of the structures a plurality of times.

Specific bias signal ranges are applicable to specific types of bias signals used in accordance with this invention. For example, electrical signals are preferably applied within a current density range of about 1 $\mu A/in^2$ to about 1000 $\mu A/in^2$ and a frequency range of about 0 Hz to about 10,000 Hz the skin surface of a recipient. Mechanical signals preferably have a displacement at the skin surface within the range of about 1 $\mu m$ to about 10 mm and frequencies within the range of about 0 Hz to about 1000 Hz. Mechanical signals can be remotely controlled by providing mechanical actuators on the skin surface that receive remotely generated waveform signals from a remote transmitter and convert these signals to mechanical signals. In wireless systems, electrical signals can also be transmitted from a remote transmitter to electrodes that apply electrical signals to a subject. All bias signals are preferably designed to allow for complex constructive and/or destructive patterns.

Naturally-occurring growth hormones, as another example, are released in humans by the pituitary gland. These hormones are part of the body's system of changing the architecture of muscle and bone in response to changes in activity. For example, increases in muscle bulk in response to exercise are partly caused by increased amounts of circulating growth hormone in the body. Recent research has established that afferent signals from the periphery, specifically those arising from muscle, spur release of specific types of growth hormone from the pituitary (McCall, et al., 2000). In accordance with the present invention, sensory feedback neurons are made more active by applying bias signals to lower the sensory cell threshold during a physical training regimen. As a result, afferent traffic from the periphery is increased, which causes neuroplastic changes in the brain. For example, sensory information from muscle spindles that boost release of growth hormone in response to activity is increased. This is especially beneficial to individuals, e.g. strength trainers, working to regain muscle bulk and bone integrity following trauma or prolonged periods of inactivity. In some cases, the increase in growth hormone release may be sufficient to eliminate the need for growth hormone replacement therapies and the need for growth hormone supplements.

Interconnections and efficiency of sensorimotor pathways in the periphery are a manifestation of the acquisition of new motor skills. That is, a key result of training and practice is the creation of these new pathways. Indeed, even increases in strength are due as much to neurologic changes as to increases in muscle mass, especially early in strength building regimens. Recent research has shown that afferent activity spurs the creation of new synapses ("synaptogenesis"), one of the underlying neurophysiologic processes of peripheral neuroplasticity (Wong, et al., 2000). Applying bias signals to an input area in accordance with the method of the present invention increases information-rich sensory traffic from the periphery drives neuroplastic changes in the periphery. A common perception of strength training is that it involves only muscularity, and that neurology is not a consideration. In actuality, neurological factors are central to the development and maintenance of muscular strength. In the initial stages of a strength training regimen, muscle mass does not increase significantly but strength does as a result of the neuromuscular learning process. By applying bias signals to an input area in accordance with the method of the present invention, the time for completing this process is significantly reduced by lowering the threshold for the sensory cells involved during this stage of the strength training. As a result, information-rich traffic from the periphery drives neuroplastic changes in the periphery that, among other things, increases the rate by which muscle mass formed.

Strength training performed in accordance with the present invention is also effective in enhancing crossover strength changes in human appendages such as the arms or the legs. Strength training research has shown that when only one appendage is subjected to a strength training regimen, the strength of the untrained appendage increases to some degree. Thus, if one appendage is immobilized by a cast or brace, the strength of the immobilized appendage can be enhanced by using the method of the present invention to lower the sensory cell thresholds in the opposite appendage during a strength training regimen for the opposite appendage.

Many athletic training programs are directed to the improvement of balance that is required when weight is rapidly transferred from side to side. Balance enhancement training regimens have included prolonged repetitive side-to-side motion to promote motor learning that results in enhanced balance. Again, in combination with this side-to-side training regimen, the present invention involves lowering affected sensory cell thresholds during the training to achieve with greater rapidity enhanced balance.

Moreover, both normal acquisition of new motor skills, and the process of regaining motor skills following injuries such as stroke, rely on the elimination and creation of new connections throughout the sensory and motor cortices. Recent research has established that sensory activity from the periphery is one of the underlying drivers of these beneficial neuroplastic changes in the brain (McKay, et al., 2002). Applying a bias signal to an input area in accordance with the method of the present invention also increases afferent traffic thereby accelerating the improvement of motor skills.

Figure 5A:
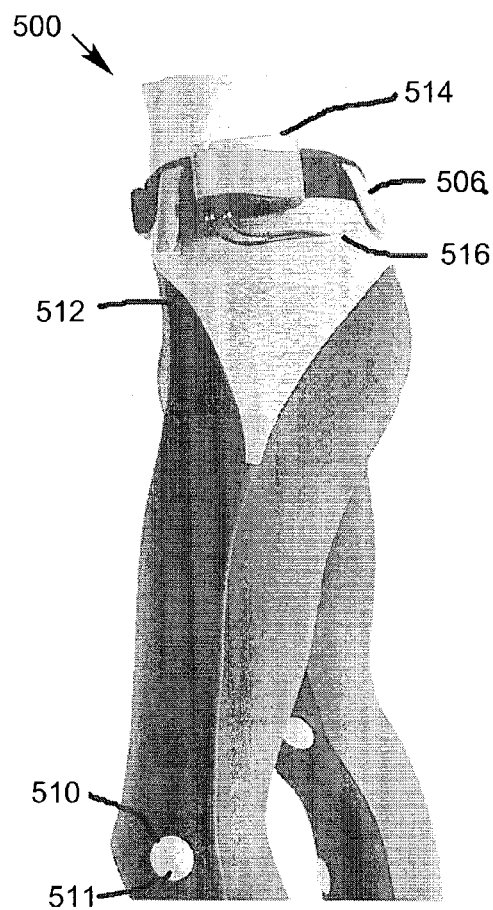
FIGS. 5A-5B illustrates an system for enhancing sensorimotor performance.
Figure 5B:
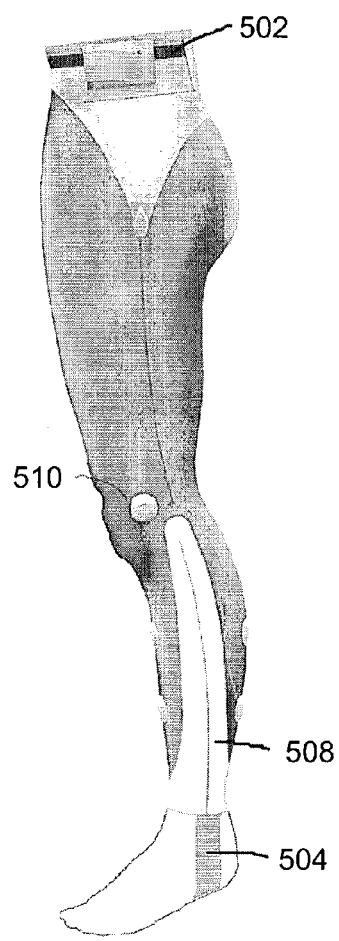

FIGS. 5A-5B, illustrate one preferred system for applying input signals in accordance with the method of the present invention as applied during a physical training regimen. The system comprises a lower extremity garment 500 that extends from the waist of a user down both legs. A belt 502 secures the garment at the waist while foot straps 504 which extend beneath the user's feet hold the garment snugly against the body during lower body motion. Foot straps are preferably composed of neoprene or other known elastic material. Garment 500 preferably includes a plurality of belt straps 506 positioned circumferentially around the waist section of the garment 500. The loose ends of straps 506 fold over belt 502 and attach to garment 500 via Velcro or other known fastening means to, in effect, form a belt-loop that securely retains belt 502 at waist level.

Garment 500 is designed for the application of input signals at and below the knee. Consequently, the legs of the garment have closures 508 that permit input device 510 to be positioned at selected positions relative to the knee, calf and/or lower leg muscles while also being maintained in place to garment 500. External caps 511 clip through the garment and onto input device 510, so as to securely hold input device 510 in place. Signal input devices 510, therefore, can be placed at virtually any position on the garment as necessary for various applications and to accommodate the anatomy of the subject. To fit garment 500 to a user, input devices 510 are first placed on the skin of a user relative to specific muscles, joints, etc. Garment 500 is then carefully donned over input devices 510 and external caps 511 are clipped through garment 500 to hold input devices 510 in place. Garment 500 is preferably formed of neoprene or any known stretchable material that enables the garment to closely conform to the subject and securely hold the input devices 510 securely against the subject's skin to prevent displacement of the input devices 510 during the prolonged motion involved in an exercise regimen.

Cables 512 electrically connect the input devices 510 to a signal generator 514. Signal generator 514 provides power to input device 510 on the inner surface of the garment so that changes in the position of the electrodes can be adjusted within the area of input devices 510. Cables 512 are preferably secured to garment 500 such that there are no loose cables to impede body movement. In a preferred embodiment, cables 512 extending from signal generator 514 are secured within side pockets 516 of garment 500. Cables 512 extend through pockets 516 into a conduit 520 that extends downward along the leg portions of garment 500. Conduit 520 branches into multiple conduits at knee level, so as to accommodate input devices 510 positioned at various positions on and about the lower leg. Input devices 510 can be attached at any position along the length of cables 512. A cable guide 522 made of plastic or similar material surround conduit 520 so as to maintain the opening of conduit 520 into pocket 516. The conduit opening maintained by cable guide 522 allows cable 512 to be fed into and out of the length of conduit 520 with considerable ease.

Cable 512 is preferably of sufficient length to permit signal generator 514 to slide from the side of belt 502 to the back of the belt 502. Thus, signal generator 514 can be repositioned at various positions along belt 502, so as not to restrict movement required by specific exercises. Signal generator 514 can also be worn at other locations or hand held. Generally, the placement of signal generator 514 is determined based upon location of the joint to be stabilized, the comfort of the subject and/or the ease of motion by the subject. To eliminate cables 512, signal generator 514 may include one or more wireless transmitters operative to transmit signals to signal generator 514 and/or input devices 510.

Figure 6:
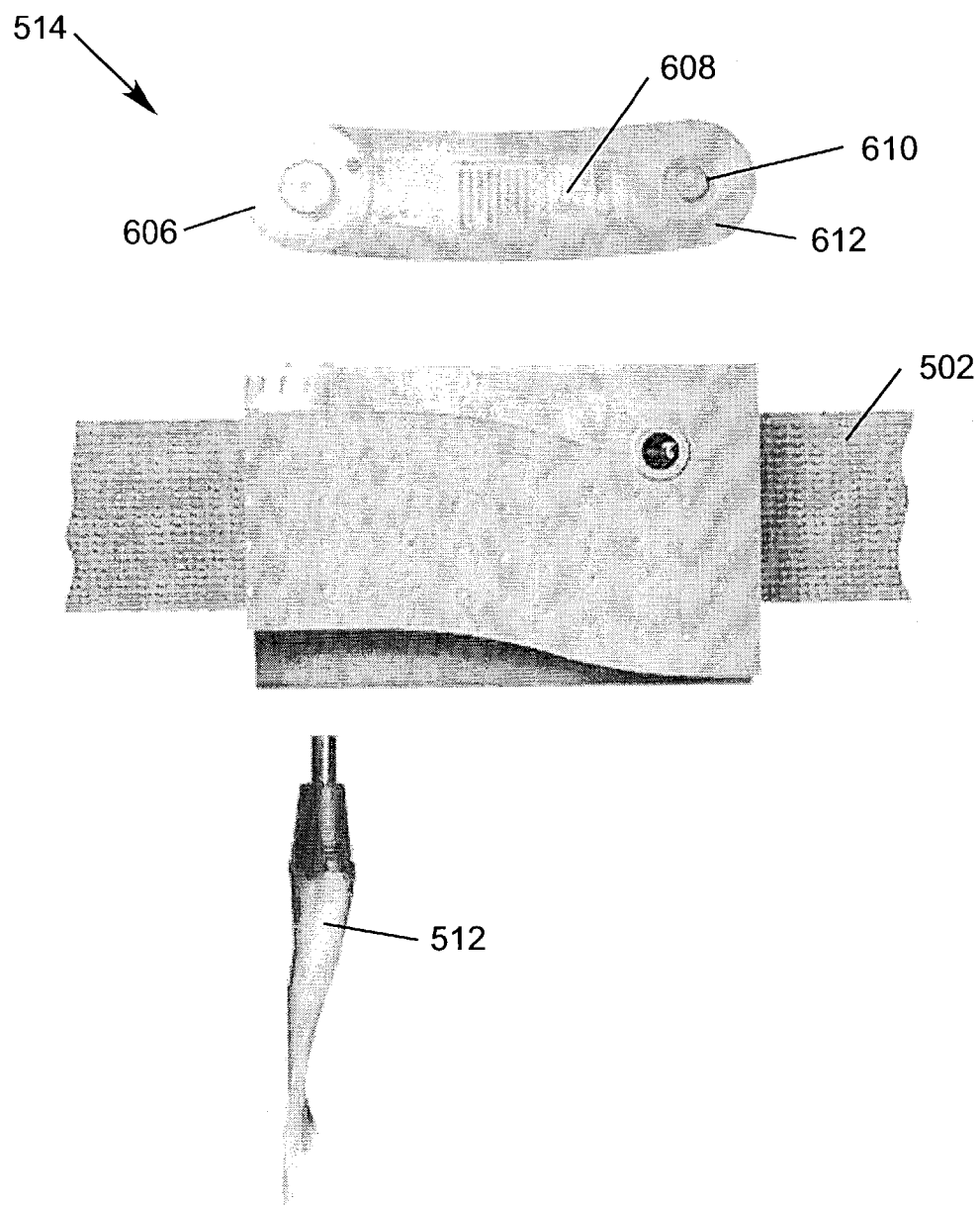
FIG. 6 is illustrates a signal generator of the present invention.

Signal generator 514, as shown in FIG. 6, includes a signal processor 404, a controller 410, control dials 606, a display 608, a test button 610, and an infrared port 612. Display 608 shows graphic information that is of interest to the user or clinician such as current stimulation program, remaining battery life, stimulation levels, active channels, errors etc. Infrared port 612 (or wireless or cabled, etc.) provides a link to a computer station that permits the downloading of custom stimulation patterns and waveforms. Test button 610 permits the confirmation of appropriate controller function. Controls dials 606 are operative to vary the amplitude of the noise signals provided to the signal input devices 510 so as to maintain the signals below the threshold level of the sensory cells targeted, as well as below the subcutaneous threshold level. The electrical current density at each signal input device 510 is determined by the current amplitude and the size of the electrode. The current density must be maintained within an acceptable range. In the case of electrical stimulation, channels may be electrically isolated from one another or may share a common ground.

Input devices 510 can apply, through the skin, input signals to the structure associated with joint orientation. As earlier noted, the input devices 510 in the garment can be surface electrodes, muscle stimulators, tendon stimulators, and magnetic field stimulators, vibratory stimulators, e.g. small electromagnetic rotary motors or flat motors (i.e. pancake motors), piezoelectric actuators, ferrofluid magnetic actuators, or electrorheologic actuators, or other known signal input device The signal input devices are appropriately sized and arranged to localize stimulation to a desired structure. For example, knee electrodes and actuators are sized as to not impede or restrict motion and to limit (target) the stimulation to the sensory neurons of interest. Signal generator 514 can be programmed to vary the intensity and timing of the signals. For example, when more than one input device 510 is used, the location and polarity of the signals can be varied. Similarly, the stimulation can simultaneously occur at each of input devices 510, or the stimulation can occur sporadically between each of input devices 510. The power and frequency of stimulation can also be controlled. The signal is at a level below the perception threshold of sensory cells associated with the various structures that play a role in the joint's stability. Thus, the signal is at a level below that required to trigger the sensory cells in those structures.

The level of the signal supplied by signal generator 514 may also be enough to stimulate other cells that are located in structures not directly involved in joint stability. For example, sensory cells within the skin may perceive a signal supplied through an input device 510 placed upon the skin, but the level is still below the threshold required to stimulate the sensory cells of the structure, e.g., such as the hamstring below the skin, which is associated with the stability of the knee joint. Such low level signals are described in Collins et al., U.S. Pat. No. 5,782,873.

Figure 7:
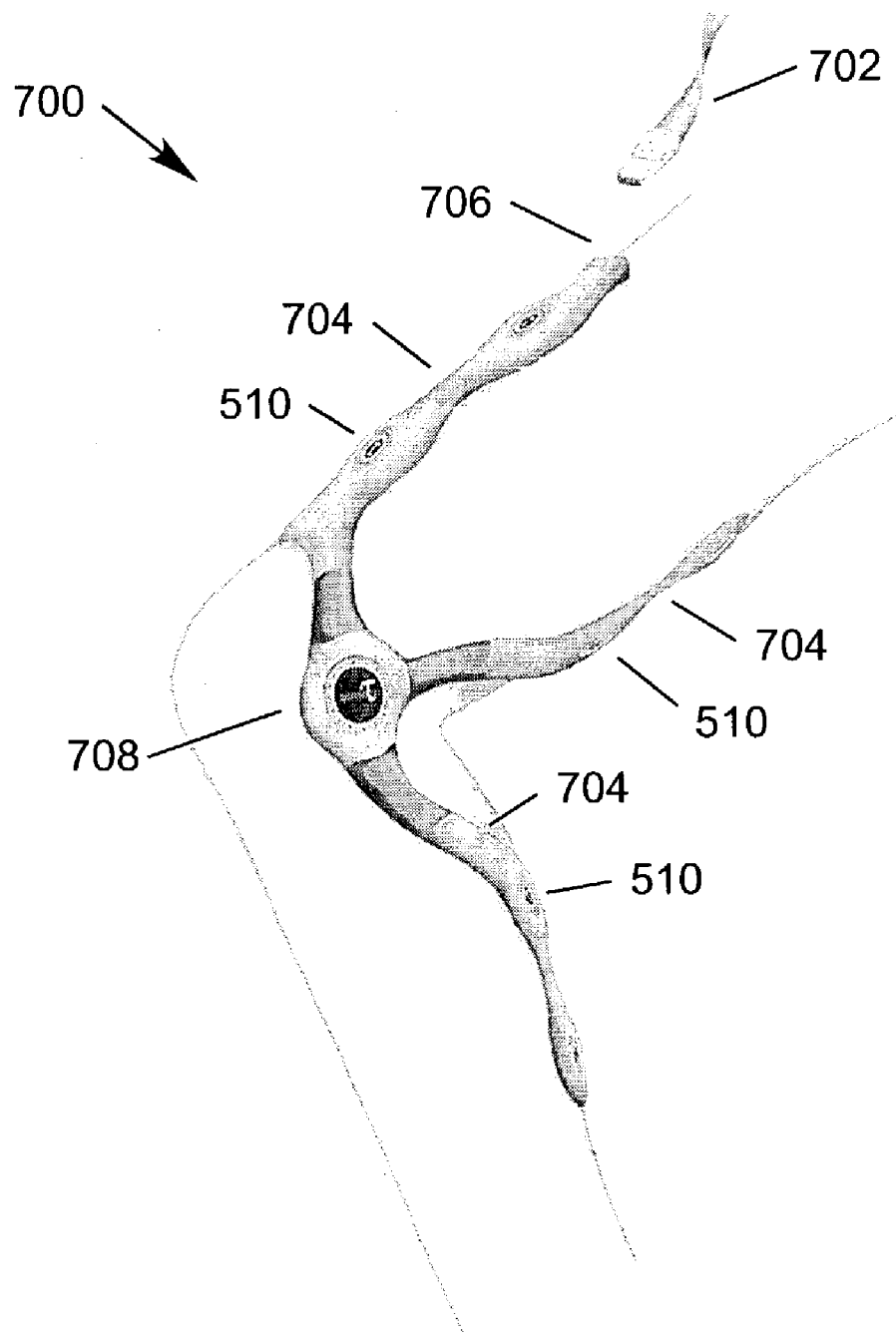
FIG. 7 illustrates wearable device, as one embodiment of the present invention.

In another preferred embodiment, provided is a structure 700 for placing signal input devices 510 in contact with the subject's skin, as shown in FIG. 7. A plurality of arms 704 extend from central hubs 708 which, when structure 700 is properly worn, are positioned on opposite sides of the joint of interest. The portion of arms 704 immediately adjacent to the central hubs 708 is composed of an expandable material, e.g. rubber. Arms 704 are preferably biased inwards inward to a degree, such as to securely engage the leg when structure 700 is positioned on the extremity. Arms 704 also include a plurality of input devices 510 positioned such that when structure 700 is properly positioned on the extremity, input devices 510 are positioned on those areas of the leg where the bias signal is to be applied in accordance with the method of the present invention.

At least one of the arms 704 includes a cable outlet 706 that is electrically wired to each of input devices 510. Outlet 706 accommodates electrical connector 702 of cable 512 such that when the other end of cable 512 is connected to signal generator 514, an electrical connection is established between signal generator 514 and input devices 510. Cable 512 is preferably composed of a stretchable and strain resistant material to reduce the likelihood of cable 512 becoming detached from outlet 706 or signal generator 514 during use.

Figure 8B:
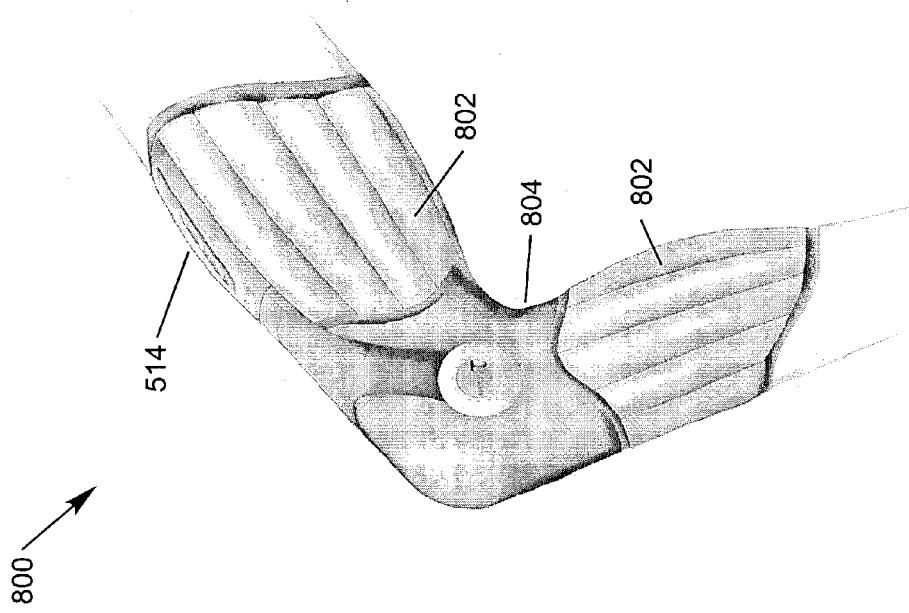
FIG. 8A-8B illustrate wearable device, as another embodiment of the present invention.
Figure 8A:
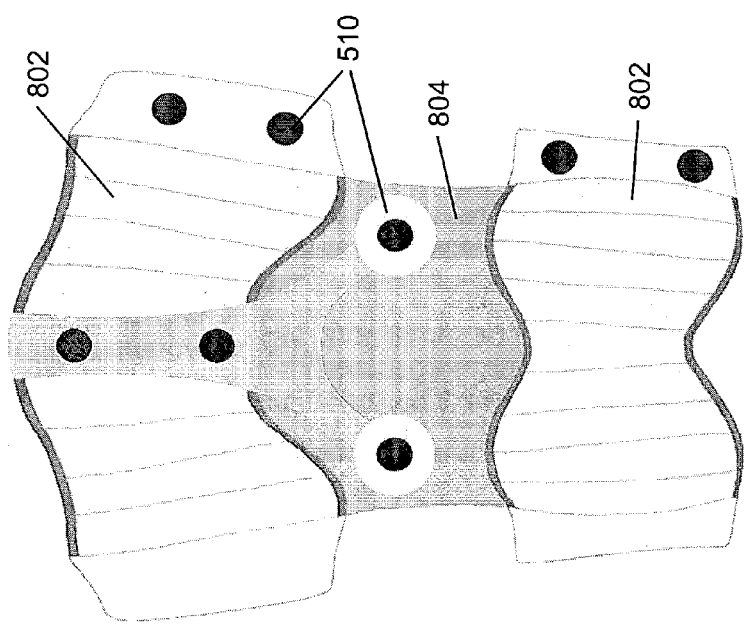

In another aspect of the invention, provided is a joint covering structure 800, as shown in FIGS. 8A-8B on a knee joint, having a plurality of input devices 510, and preferably a signal generator 514, incorporated into or positioned thereon. Input devices 510 are positioned so as to engage the appropriate combination of muscles and joints to which the bias signal is to be applied in accordance with the method of the present invention. Joint structure 800 is preferably designed to wrap around the joint and fasten upon itself by Velcro or other known fastening means. Alternatively, joint structure 800 can be configured to slide onto and off of the joint. Joint structure 800 is preferably made of fabric, but can also be made of plastic, rubber, or other material, as long as at least a portion of the structure is made of a flexible material which allows the input devices 510 to remain in place during the flexing and extending of the joint. As illustrated, the ridged portion 802 of structure 800 is comprised of thicker material capable of assistively bracing the joint. A thinner portion 804 of structure 800 is positioned over the joint so as to allow bending of the joint without displacing the input devices 510.

Figure 9:
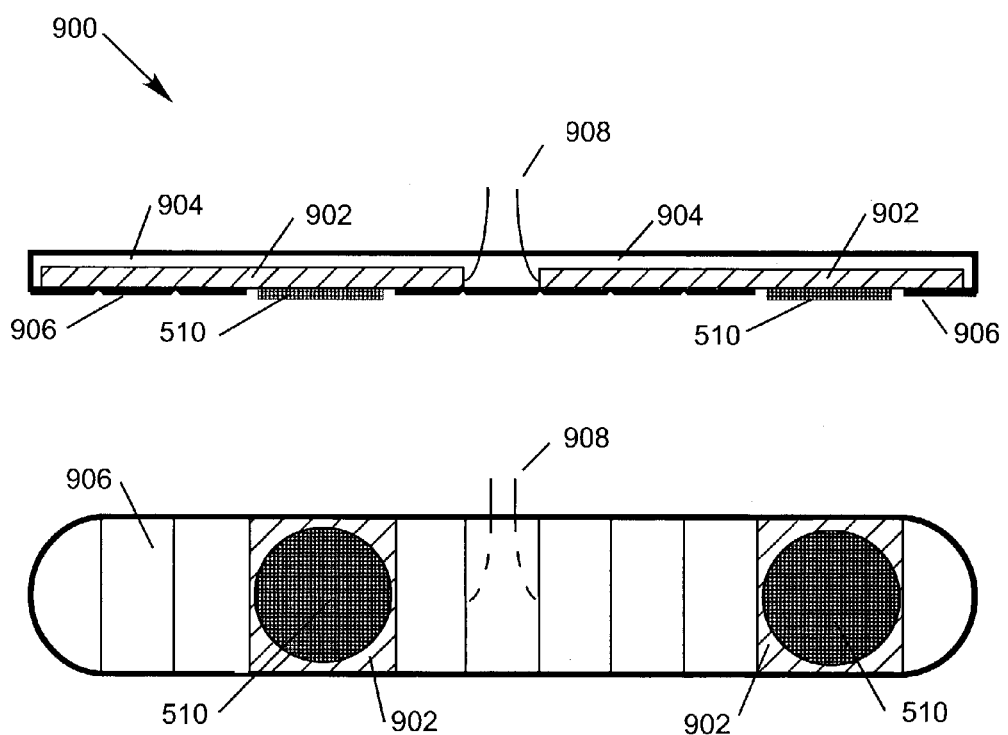
FIG. 9 illustrates a signal input device of the present invention.

In another aspect of the invention, provided is an electrode applicator 900, as shown in FIG. 9, which provides a means to customize the position of, or distance between, signal input devices 510 (e.g. skin surface electrodes) for a subject receiving treatment in accordance with the method of present invention. Areas of flexible, electrically conductive layer 902, such as conductive rubber, provide an electrically conductive means between wires 908 and signal input devices 510. Covering and surrounding the conductive layer 902 on the outer surface of the structure is a non-conductive material 904. These two layers of conductive 902 and non-conductive materials 904 are permanently affixed to one another. Also covering conductive layer 902 on its inner, or skin surface, side is a non-conductive film 906 which is removably affixed to the conductive layer 902. By removing non-conductive film 906, the inner surface of conductive layer 902 is exposed, allowing a signal input device 510 to be affixed to the conductive layer 902. Non-conductive film 906 is scored or otherwise segmented in a pattern which allows for portions of the non-conductive film 906, rather than the entire film, to be removed. In this way, the majority of the conductive layer 902 remains covered by the non-conductive film 906 during use. Signal input devices 510 are composed of a thin, electrically conductive material, such as hydrogel, that provides the electrical interface between the conductive layer 902 and the subject's skin.

The apparatus used for performing the method of the present invention is unique relative to known units used for improving sensorimotor performance (e.g. motor learning) or the treatment of injuries and rehabilitation from the effect of an injury. In such known units, electrodes are mounted on braces or wraps and include free, untethered electrical conductors, all of which will inhibit the motion required for the performance of an effective physical training regimen.

While the above illustrated embodiments are directed to pants, a joint stabilizer, and a brace, the term wearable device as used herein, refers to any structure capable of holding input devices 510 in place at a desired location.

The embodiments described herein have been shown as a lower body wearable device for illustrative purposes only. Similar embodiments capable of holding signal input devices in place that are designed to the upper body including the arms and torso of an individual, are within the spirit and scope of present invention. The upper body wearable device may be combined with the lower body wearable device to permit input devices to be positioned and operated simultaneously along both the upper and lower body in accordance with the method of the invention.

Although the present invention has been described in detail, it should be understood that various changes, substitutions, and alterations can be made without departing from the intended scope as defined by the appended claims.

What is claimed is:

1. A method of enhancing sensorimotor performance in a subject comprising the steps of:
   inputting at least one bias signal to at least one sensory cell area of said subject;
   moving at least one body segment of said subject relative to another simultaneous with said inputting at least one bias signal to at least one sensory cell area of said subject, wherein said at least one body segment utilizes sensory cells within said sensory cell area that is involved in the sensorimotor performance to be enhanced; and
   inducing neuroplastic changes in the nervous system of said subject by inputting said at least one bias signal for a period of time long enough that said subject's sensorimotor performance is enhanced.

2. The method of claim 1, wherein said sensorimotor performance to be enhanced is joint stability, and inputting the at least one bias signal to at least one sensory cell area that is involved in the subject's joint stability.

3. The method of claim 1, wherein said sensorimotor performance to be enhanced is gait, and inputting the at least one bias signal to at least one sensory cell area that is involved in the subject's gait.

4. The method of claim 1, wherein said sensorimotor performance to be enhanced is balance, and inputting the at least one bias signal to at least one sensory cell area that is involved in the subject's standing balance.

5. The method of claim 1, wherein said sensorimotor performance to be enhanced is motor learning, and inputting the at least one bias signal to at least one sensory cell area that is involved in the subject's motor learning.

6. The method of claim 1, wherein said sensorimotor performance to be enhanced is motor skill, and inputting the at least one bias signal to at least one sensory cell area that is involved in the subject's motor skill.

7. The method of claim 1, wherein said neuroplastic changes are neuroplastic changes in the central nervous system.

8. The method of claim 1, wherein said neuroplastic changes are neuroplastic changes in the peripheral nervous system.

9. The method of claim 1, further comprising the step of modulating said bias signal in synchrony with said moving of at least one body segment.

10. The method of claim 1, further comprising the steps of:
    measuring a physical variable from at least one body segment of said subject during said moving of said at least one body segment pre-defined physical activity, wherein said physical variable is selected from the group consisting of force, pressure, position, angle, velocity, and acceleration; and
    modulating said bias signal in response to at least one of said physical variables.

11. The method of claim 1, wherein said bias signal is a mechanical signal having a displacement of about 1 μm to about 10 mm.

12. The method of claim 1, wherein said bias signal is a mechanical signal composed of one or more frequencies within the range of about 0 Hz to about 1000 Hz.

13. The method of claim 1, wherein said bias signal is a electrical signal having a current density in the range of about 1 $\mu A/in^2$ to about 1000 $\mu A/in^2$.

14. The method of claim 1, wherein said bias signal is an electrical signal composed of one or more frequencies within the range of about 0 Hz to about 10,000 Hz.

15. A method of enhancing sensorimotor performance in a subject comprising the step of:
    generating at least one bias signal using a system for enhancing sensorimotor performance, said system comprising a wearable device to which at least one signal input device is repositionably secured, and a signal generator communicatively coupled to said at least one signal input device for generating said bias signal;

inputting at least one bias signal to at least one sensory cell area of said subject;

moving at least one body segment of said subject relative to another simultaneous with said inputting at least one bias signal to at least one sensory cell area of said subject, wherein said at least one body segment utilizes sensory cells within said sensory cell area that is involved in the sensorimotor performance to be enhanced;

inducing neuroplastic changes in the nervous system of said subject by inputting said at least one bias signal for a period of time long enough that said subject's sensorimotor performance is enhanced.

16. The method of claim 15, wherein said sensorimotor performance to be enhanced is joint stability, and inputting the at least one bias signal to at least one sensory cell area that is involved in the subject's joint stability.

17. The method of claim 15, wherein said sensorimotor performance to be enhanced is gait, and inputting the at least one bias signal to at least one sensory cell area that is involved in the subject's gait.

18. The method of claim 15, wherein said sensorimotor performance to be enhanced is standing balance, and inputting the at least one bias signal to at least one sensory cell area that is involved in the subject's standing balance.

19. The method of claim 15, wherein said sensorimotor performance to be enhanced is motor learning, and inputting the at least one bias signal to at least one sensory cell area that is involved in the subject's motor learning.

20. The method of claim 15, wherein said sensorimotor performance to be enhanced is motor skill, and inputting the at least one bias signal to at least one sensory cell area that is involved in the subject's motor skill.

21. The method of claim 15, wherein said neuroplastic changes are neuroplastic changes in the central nervous system.

22. The method of claim 15, wherein said neuroplastic changes are neuroplastic changes in the peripheral nervous system.

23. The method of claim 15, further comprising the step of modulating said bias signal in synchrony with said moving of at least one body segment.

24. The method of claim 15, further comprising the steps of:
measuring a physical variable from at least one body segment of said subject during said moving of at least one body segment, wherein said physical variable is selected from the group consisting of force, pressure, position, angle, velocity, and acceleration; and
modulating said bias signal in response to said physical variable.

25. The method of claim 15, wherein said bias signal is a mechanical signal having a displacement of about 1 µm to about 10 mm.

26. The method of claim 15, wherein said bias signal is a mechanical signal composed of one or more frequencies within the range of about 0 Hz to about 1000 Hz.

27. The method of claim 15, wherein said bias signal is an electrical signal having a current density in the range of about 1 µA/in$^2$ to about 1000 µA/in$^2$.

28. The method of claim 15, wherein said bias signal is an electrical signal composed of one or more frequencies within the range of about 0 Hz to about 10,000 Hz.

29. A method of improving neurological function in a subject comprising the step of:
inputting at least one bias signal to at least one sensory cell area of a subject;
moving at least one body segment of said subject relative to another simultaneous with said inputting at least one bias signal to at least one sensory cell area of said subject, wherein said at least one body segment utilizes sensory cells within said sensory cell area that is involved in the sensorimotor performance to be enhanced;
inducing neuroplastic changes in the nervous system of said subject by inputting said at least one bias signal for a period of time long enough that said subject's sensorimotor performance is enhanced.

30. A method of improving neurological function in a subject comprising the step of:
generating at least one bias signal using a system for enhancing neurological function, said system comprising a wearable device to which at least one signal input device is repositionably secured, and a signal generator communicatively coupled to said at least one signal input device for generating said bias signal;
inputting at least one bias signal to at least one sensory cell area of said subject;
moving at least one body segment of said subject relative to another simultaneous with said inputting at least one bias signal to at least one sensory cell area of said subject, wherein said at least one body segment utilizes sensory cells within said sensory cell area that is involved in the sensorimotor performance to be enhanced;
inducing neuroplastic changes in the nervous system of said subject by inputting said at least one bias signal for a period of time long enough that said subject's sensorimotor performance is enhanced.

31. The method of claim 29, wherein said neurological function is sensorimotor performance.

32. The method of claim 31, wherein said sensorimotor performance to be enhanced is joint stability, and inputting the at least one bias signal to at least one sensory cell area that is involved in the subject's joint stability.

33. The method of claim 31, wherein said sensorimotor performance to be enhanced is gait, and inputting the at least one bias signal to at least one sensory cell area that is involved in the subject's gait.

34. The method of claim 31, wherein said sensorimotor performance to be enhanced is standing balance, and inputting the at least one bias signal to at least one sensory cell area that is involved in the subject's standing balance.

35. The method of claim 31, wherein said sensorimotor performance to be enhanced is motor learning, and inputting the at least one bias signal to at least one sensory cell area that is involved in the subject's motor learning.

36. The method of claim 31, wherein said sensorimotor performance to be enhanced is motor skill, and inputting the at least one bias signal to at least one sensory cell area that is involved with the subject's motor skill.

37. The method of claim 29, wherein said neurological changes are in the central nervous system.

38. The method of claim 29, further comprising the step of measuring said neuroplastic changes.

39. The method of claim 29, wherein said moving is performed voluntarily by said subject.

40. The method of claim 29, wherein said moving is performed by another.

41. The method of claim 29, wherein said moving is performed by a machine.

42. The method of claim 29, wherein said moving is conducted as part of a physical training regimen.

43. The method of claim 42, wherein said physical training is a prescribed physical training regimen.

44. The method of claim 29, wherein said body segment is a skeletal body segment.

45. The method of claim 30, wherein said improved neurological function is sensorimotor performance.

46. The method of claim 45, wherein said sensorimotor performance to be improved is joint stability, and inputting the at least one bias signal to at least one sensory cell area that is involved in the subject's joint stability.

47. The method of claim 45, wherein said sensorimotor performance to be enhanced is gait, and inputting the at least one bias signal to at least one sensory cell area that is involved in the subject's gait.

48. The method of claim 45, wherein said sensorimotor performance to be enhanced is standing balance, and inputting the at least one bias signal to at least one sensory cell area that is involved in the subject's standing balance.

49. The method of claim 45, wherein said sensorimotor performance to be enhanced is motor learning, and inputting the at least one bias signal to at least one sensory cell area that is involved in the subject's motor learning.

50. The method of claim 45, wherein said sensorimotor performance to be enhanced is motor skill, and inputting the at least one bias signal to at least one sensory cell area that is involved in the subject's motor skill.

51. The method of claim 30, wherein said neurological changes are in the central nervous system.

52. The method of claim 30, wherein said neurological changes are in the peripheral nervous system.

53. The method of claim 30, further comprising the step of measuring said neuroplastic changes.

54. The method of claim 30, wherein said moving is performed voluntarily by said subject.

55. The method of claim 30, wherein said moving is performed by another.

56. The method of claim 30, wherein said moving is performed by a machine.

57. The method of claim 30, wherein said moving is conducted as part of a physical training regimen.

58. The method of claim 57, wherein said physical training is a prescribed physical training regimen.

59. The method of claim 30, wherein said body segment is a skeletal body segment.

60. A method of enhancing sensorimotor performance comprising the steps of:
   instructing a subject to move at least one body segment which utilizes sensory cells within at least one sensory cell area that is involved in the sensorimotor performance to be enhanced;
   inputting at least one bias signal to at least one sensory cell area of a subject simultaneous with the subject moving at least one body segment;
   inducing neuroplastic changes in the nervous system of said subject by inputting said bias signal for a time period long enough to enhance said subject's sensorimotor performance.

61. The method of claim 60, wherein said sensorimotor performance to be enhanced is joint stability, and inputting the at least one bias signal to at least one sensory cell area that is involved in the subject's joint stability.

62. The method of claim 60, wherein said sensorimotor performance to be enhanced is gait, and inputting the at least one bias signal to at least one sensory cell area that is involved in the subject's gait.

63. The method of claim 60, wherein said sensorimotor performance to be enhanced is standing balance, and inputting the at least one bias signal to at least one sensory cell area that is involved in the subject's standing balance.

64. The method of claim 60, wherein said sensorimotor performance to be enhanced is motor learning, and inputting the at least one bias signal to at least one sensory cell that is involved in the subject's motor learning.

65. The method of claim 60, wherein said sensorimotor performance to be enhanced is motor skill, and inputting the at least one bias signal to at least one sensory cell area that is involved in the subject's motor skill.

66. The method of claim 60, wherein said neuroplastic changes are neuroplastic changes in the central nervous system.

67. The method of claim 60, wherein said neuroplastic changes are neuroplastic changes in the peripheral nervous system.

68. The method of claim 60, further comprising the step of modulating said bias signal in synchrony with said moving of at least one body segment.

69. The method of claim 60, further comprising the steps of:
   measuring a physical variable from at least one body segment of said subject during said moving of said at least one body segment wherein said physical variable is selected from the group consisting of force, pressure, position, angle, velocity, and acceleration; and
   modulating said bias signal in response to at least one of said physical variables.

70. The method of claim 60, wherein said bias signal is a mechanical signal having a displacement of about 1 µm to about 10 mm.

71. The method of claim 60, wherein said bias signal is a mechanical signal composed of one or more frequencies within the range of about 0 Hz to about 1000 Hz.

72. The method of claim 60, wherein said bias signal is an electrical signal having a current density in the range of about 1 µA/in$^2$ to about 1000 µA/in$^2$.

73. The method of claim 60, wherein said bias signal is an electrical signal composed of one or more frequencies within the range of about 0 Hz to about 10,000 Hz.

74. The method of claim 60, further comprising the step of measuring said neuroplastic changes.

75. The method of claim 60, wherein said moving is conducted as part of a physical training regimen.

76. The method of claim 75, wherein said physical training is a prescribed physical training regimen.

77. The method of claim 60, wherein said body segment is a skeletal body segment.

78. The method of claim 1, further comprising the step of measuring said neuroplastic changes.

79. The method of claim 1, wherein said moving is performed voluntarily by said subject.

80. The method of claim 1, wherein said moving is performed by another.

81. The method of claim 1, wherein said moving is performed by a machine.

82. The method of claim 1, wherein said moving is conducted as part of a physical training regimen.

83. The method of claim 82, wherein said physical training is a prescribed physical training regimen.

84. The method of claim 1, wherein said body segment is a skeletal body segment.

85. The method of claim 15, further comprising the step of measuring said neuroplastic changes.

86. The method of claim 15, wherein said moving is performed voluntarily by said subject.

87. The method of claim 15, wherein said moving is performed by another.

88. The method of claim 15, wherein said moving is performed by a machine.

89. The method of claim 15, wherein said moving is conducted as part of a physical training regimen.

90. The method of claim 89, wherein said physical training is a prescribed physical training regimen.

91. The method of claim 15, wherein said body segment is a skeletal body segment.

92. The method of claim 15, wherein said sensorimotor performance to be enhanced is reaching, and inputting the at least one bias signal to at least one sensory cell area that is involved in reaching.

93. The method of claim 15, wherein said sensorimotor performance is grasping, and inputting the at least one bias signal to at least one sensory cell area that is involved in grasping.

94. The method of claim 1, wherein said sensorimotor performance to be enhanced is reaching, and inputting the at least one bias signal to at least one sensory cell area that is involved in reaching.

95. The method of claim 1, wherein said sensorimotor performance to be enhanced is gasping, and inputting the at least one bias signal to at least one sensory cell area that is involved in grasping.

96. The method of claim 29, wherein said sensorimotor performance to be enhanced is reaching, and inputting the at least one bias signal to at least one sensory cell area that is involved in reaching.

97. The method of claim 29, wherein said sensorimotor performance is grasping, and inputting the at least one bias signal to at least one sensory cell area that is involved in grasping.

98. The method of claim 30, wherein said sensorimotor performance to be enhanced reaching, and inputting the at least one bias signal to at least one sensory cell area that is involved in reaching.

99. The method of claim 30, wherein said sensorimotor performance is grasping, and inputting the at least one bias signal to at least one sensory cell area that is involved in grasping.

100. The method of claim 60, wherein said sensorimotor performance to be enhanced reaching, and inputting the at least one bias signal to at least one sensory cell area that is involved in reaching.

101. The method of claim 60, wherein said sensorimotor performance is gasping, and inputting the at least one bias signal to at least one sensory cell area that is involved in grasping.

\* \* \* \* \*